(12) United States Patent
Cutolo et al.

(10) Patent No.: US 6,181,105 B1
(45) Date of Patent: Jan. 30, 2001

(54) SELF CONTAINED TRANSPORTABLE POWER SOURCE MAINTENANCE AND CHARGE

(75) Inventors: Vincent Cutolo, Miami; Oscar Jimenez, Coral Gables; Roberto Echarri; Guillermo Echarri, both of Miami; Francisco Jose Barreras, Sr., Miami Beach, all of FL (US)

(73) Assignee: Exonix Corporation, Miami, FL (US)

( * ) Notice: Under 35 U.S.C. 154(b), the term of this patent shall be extended for 0 days.

(21) Appl. No.: 09/414,476

(22) Filed: Jul. 9, 1999

Related U.S. Application Data

(63) Continuation-in-part of application No. 09/299,852, filed on Apr. 26, 1999, now abandoned.

(51) Int. Cl.$^7$ .................................................. H01M 10/46
(52) U.S. Cl. ............................................................ 320/115
(58) Field of Search .................................... 320/112, 113, 320/114, 115

(56) References Cited

U.S. PATENT DOCUMENTS

| 4,674,509 | * | 6/1987 | Decote, Jr. . | |
| 5,811,959 | * | 9/1998 | Kejha | 320/126 |

* cited by examiner

*Primary Examiner*—Edward H. Tso
(74) *Attorney, Agent, or Firm*—Thomas R. Vigil

(57) ABSTRACT

The power source maintenance and charge system comprises: charge maintenance circuitry for maintaining a desired charge on or for charging, a special power source of a packaged device; control circuit for actuating and de-actuating the charge maintenance circuitry; and coupling circuitry for coupling the charge maintenance circuitry to the power source including a polymer insulated flat ribbon cable that passes through one of a sterile or non-sterile sealed plastic package containing the device to connect an auxiliary power source of the charge maintenance circuitry to the special power source of the device.

23 Claims, 10 Drawing Sheets

MAGNETIC-ELECTRIC CHARGE ACTIVATION

ELECTRO-MECHANICAL CHARGE ACTIVATION *1

OPTO-ELECTRIC CHARGE ACTIVATION

ELECTRO-MECHANICAL CHARGE ACTIVATION *2

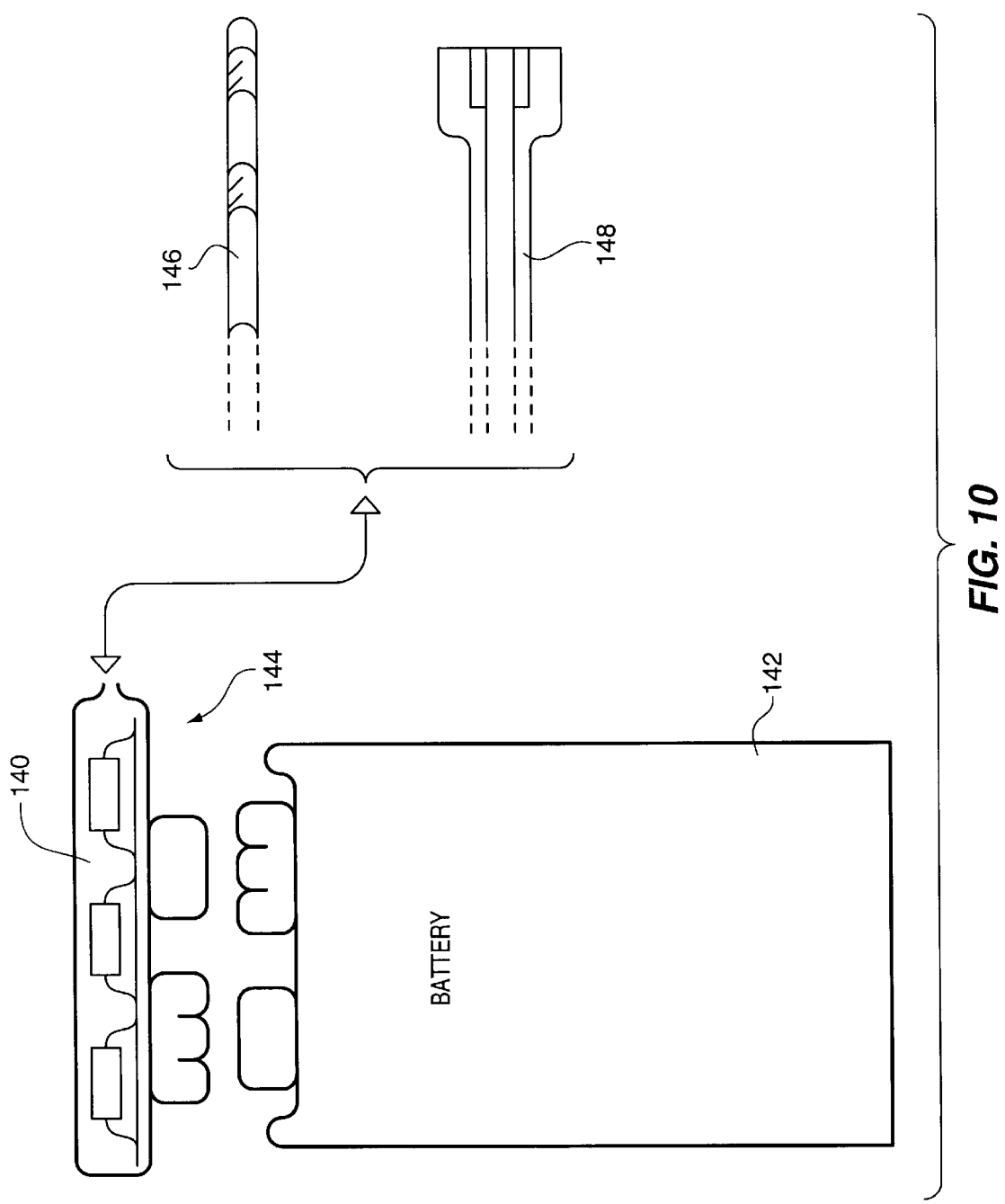

SELF CONTAINED TRANSPORTABLE POWER SOURCE MAINTENANCE AND CHARGE

This is a CIP of U.S. application Ser. No. 09/299,852 filed Apr. 26, 1999 now abandoned.

BACKGROUND OF THE INVENTION

1. Field of the Invention

The present invention relates to a self contained transportable power source maintenance and charge system for an implantable medical device encased in a sterile package. More specifically, the system includes a ribbon cable on a sterile plastic or blister package containing an implantable medical device. The system is connected to the ribbon cable, which in turn is coupled to the medical device, whereby a desired maintenance charge can be maintained on a battery of the medical device until the sterile package is opened for implanting the device.

Rechargeable lithium ion batteries are known for their high voltage and high energy density. Compared to nickel cadmium or nickel metal hydride batteries, lithium ion batteries contain 1.5 times more capacity, 3 times higher voltage with 1.5 to 2 times less weight. Unlike other rechargeable batteries, lithium ion batteries do not exhibit a memory effect, they are friendly to the environment and may be recharged in excess of 500 cycles while retaining acceptable capacity.

Another desirable feature of a lithium ion battery is that properly charged and discharged, lithium ion batteries do not produce gases; hence, they could be enclosed in a hermetically sealed enclosure.

With these attractive technical features in mind, lithium ion batteries may be utilized to power implantable devices.

Nevertheless, certain rechargeable lithium ion electrochemical cells and batteries require a specific voltage and or charge capacity control during storage or transit in order to preserve cell functional integrity. Due to cell chemistry, the cells exhibit a self discharge rate that may over time reduce the voltage down to a detrimental level. If the cell's voltage is allowed to discharge below a specific threshold voltage, prior to charging, the cell's ability to be recharged to the maximum specified capacity may be permanently lost. This loss of recharge capacity is usually referred to as faded capacity. Further, if the cell's voltage is allowed to drop to near zero volts, the cell's ability to be recharged at all may be permanently lost, rendering the cell useless. A known electrochemical mechanism that could cause irreversible damage to a lithium ion cell is dissolution of the current collector material upon voltage reduction below certain threshold.

Therefore, it becomes desirable to have a self contained transportable power source maintenance and charge system that can be pre-programmed to maintain a specific voltage and/or charge capacity of a power source, such as a lithium or any other rechargeable secondary power sources, that is affected by self discharge and its consequential damage.

2. Description of the Prior Art

Heretofore various battery power source charging systems have been proposed. Examples of some of these previously proposed systems are disclosed in the following U.S. patents:

| U.S. Pat. No. | Patentee |
|---|---|
| 5,411,537 | Munshi et al. |
| 5,631,537 | Armstrong |
| 5,670,862 | Lewyn |
| 5,675,235 | Nagai |
| 5,764,030 | Gaza |
| 5,811,959 | Kejha |
| 5,818,199 | Beard |
| 5,880,576 | Nagai |

SUMMARY OF THE INVENTION

The self contained transportable power source maintenance and charge system of the present invention uses an auxiliary power source and circuitry for delivering energy at a regulated voltage or capacity to a battery of a medical device to compensate for the inherent self discharge manifested by rechargeable power sources over storage or transit time.

The power source maintenance and charge system also provides a safe voltage or charge level for lithium ion cells and for devices that are powered by such a power source during storage or transit.

Further, the power source maintenance and charge system can safely switch from a maintenance mode to a charge mode by activating a Reed switch with a remote magnet or actuating a mechanical switch or other means thereby increasing the regulated maintenance voltage to a higher specified charging voltage. The charge activation using an electro-mechanical switch or Reed switch can be achieved inside a device's sterile blister package in order to prevent opening of the blister which may violate sterility. This feature also facilitates charging the device prior to implant without opening the sterile blister package.

BRIEF DESCRIPTION OF THE DRAWINGS

FIG. 10 is a plan view of an electronic module containing the power source maintenance and charge system integral with a battery connector adapted to be coupled to a pacing lead or to a ribbon cable as shown.

DESCRIPTION OF THE PREFERRED EMBODIMENT(S)

Figure 1:
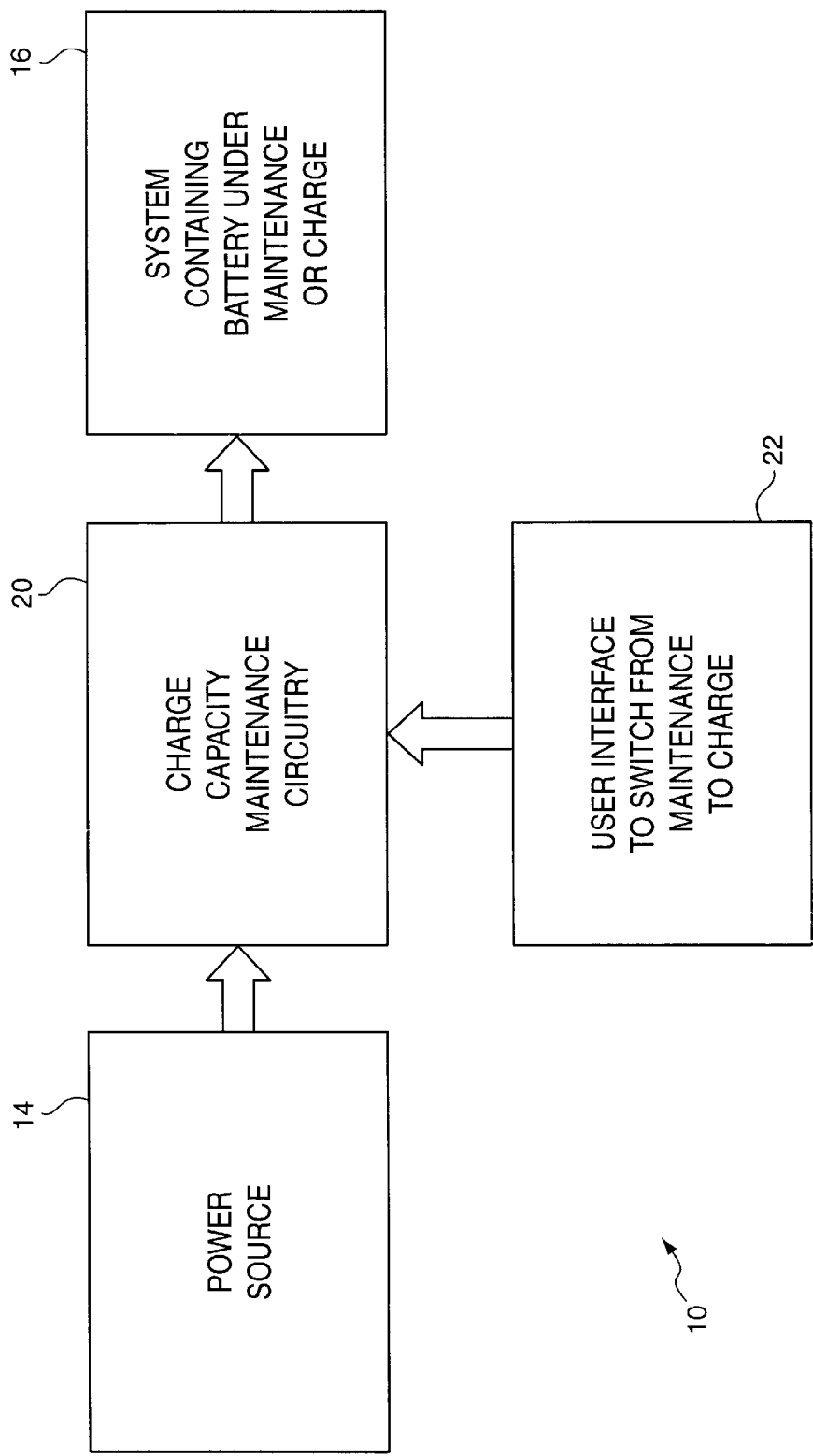
FIG. 1 is a block diagram of the power source maintenance and charge system of the present invention.
Figure 2:
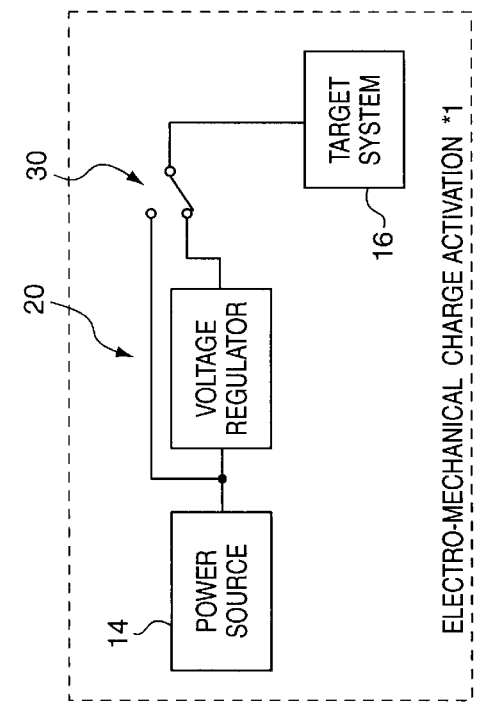
FIG. 2 is a block schematic diagram of one embodiment of a self contained transportable power source maintenance and charge system which utilizes a Reed switch and a magnet and which is constructed according to the teachings of the present invention.
Figure 3:
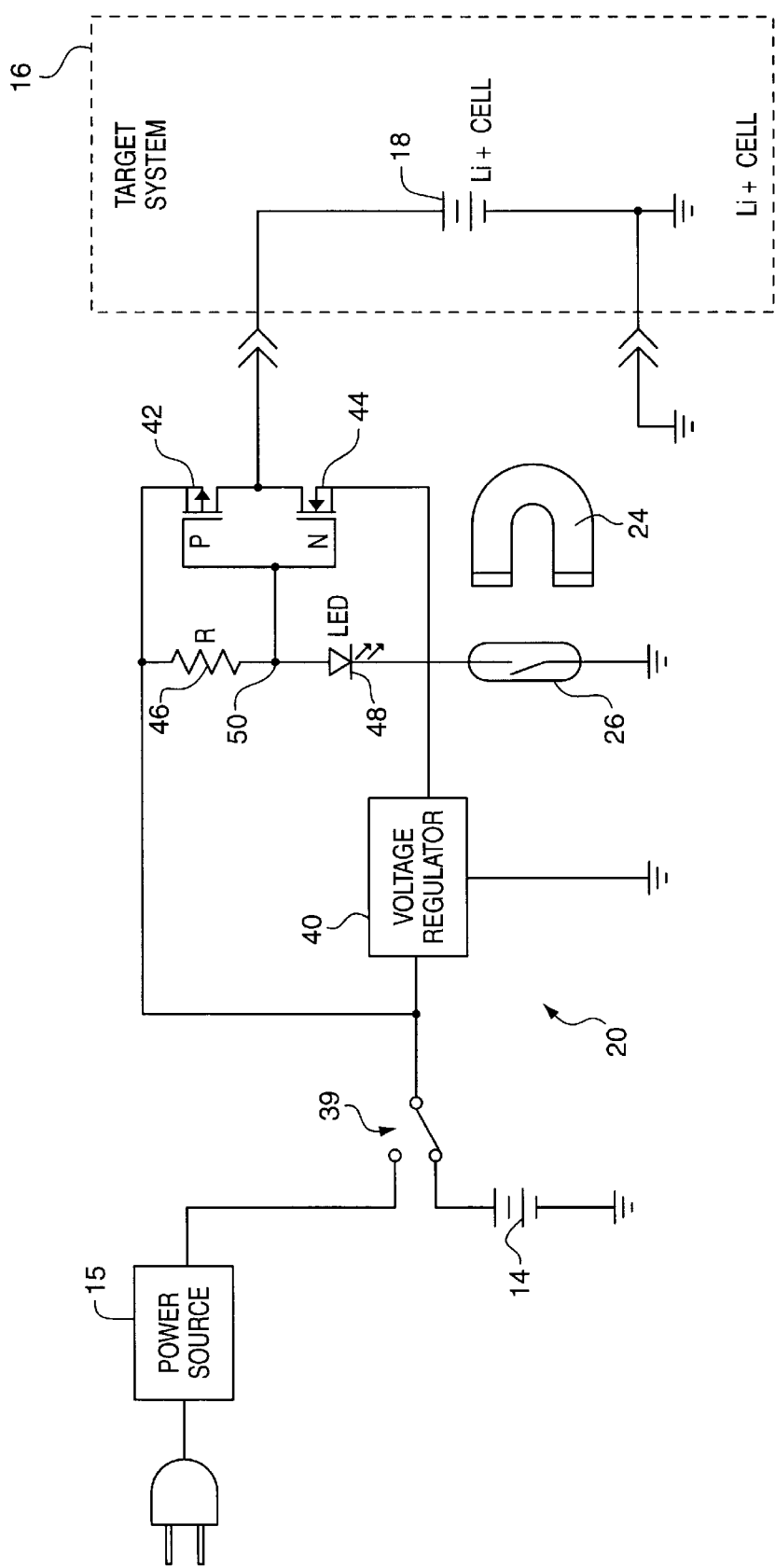
FIG. 3 is a more detailed electrical schematic diagram of the power source maintenance and charge system shown in FIG. 1 which utilizes a Reed switch.

The power source maintenance and charge system of the present invention is identified by reference numeral 10 in FIG. 1 and is capable of being used in conjunction with a polymer insulated flat ribbon cable that passes through a sterile or non-sterile double sealed blister package 12 (FIG. 7) to connect an auxiliary power source 14 (FIGS. 2–7) of the power maintenance and charge system 10 that in turn is connected to a medical device 16 (FIGS. 1–7) containing a lithium ion rechargeable cell or battery 18 (FIG. 3).

The secondary battery maintenance and charge system 10 is capable of preserving power source integrity in storage cells 18 or devices containing a lithium ion chemistry system or other power sources whereby the capacity and/or voltage is not allowed to drop below certain safe capacity and/or voltage threshold(s).

Further, the system 10 allows the power source maintenance and/or charge to take place while the device 16 is contained within a sterile blister package 12 or multiple sterile or non-sterile package 12.

The power source maintenance and charge system 10 is self contained and transportable within a sterile or non-sterile device package or blister package 12 such that the power source 18 integrity is maintained within certain safe capacity or voltage threshold during storage or transit.

The power source maintenance and charge system 10 may be switched to either maintain or charge the power source 18 within a single sterile package or sterile double blister package 12 without violating the blister package seal in order to preserve device 16 sterility. The power source maintenance and charge system 10 can be configured to maintain or configured to charge the power source 10 or other power device in the target system 16 using several methods, but not limited to any such method as follows:

(a) Activation of a Reed switch circuit 22 including a magnet 24 and Reed switch 26 as shown in FIGS. 2 and 3.

Figure 4:
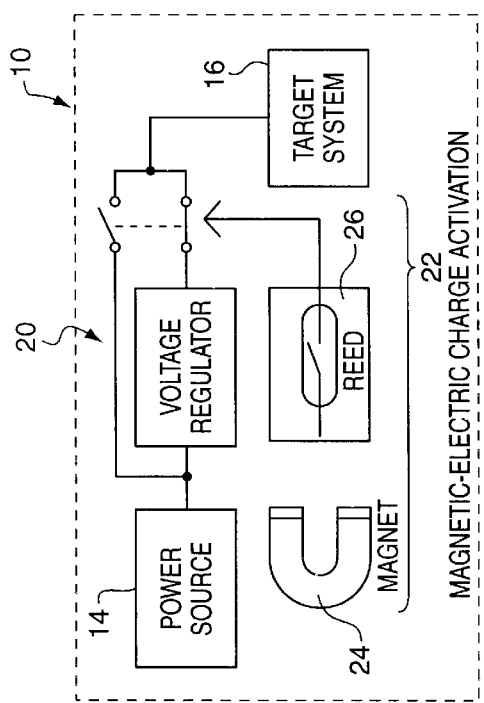
FIG. 4 is a block schematic circuit diagram, similar to the diagram of FIG. 2, of a self contained transportable power source maintenance and charge system which includes an opto-electrical charge activation circuit.

(b) Activation of a photo-optical switch circuit 28 as shown in FIG. 4.

Figure 5:
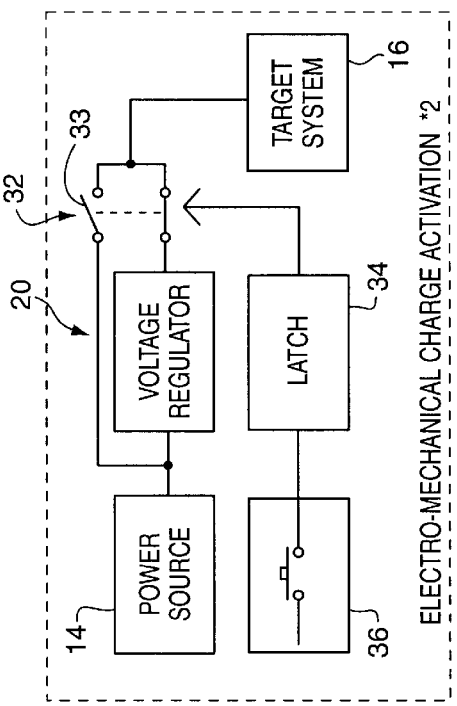
FIG. 5 is a block schematic circuit diagram, similar to the diagram of FIG. 4, of a self contained transportable power source maintenance and charge system which includes an electro-mechanical charge activation system.

(c) Activation of an electro-mechanical switch circuit 30 as shown in FIG. 5.

Figure 6:
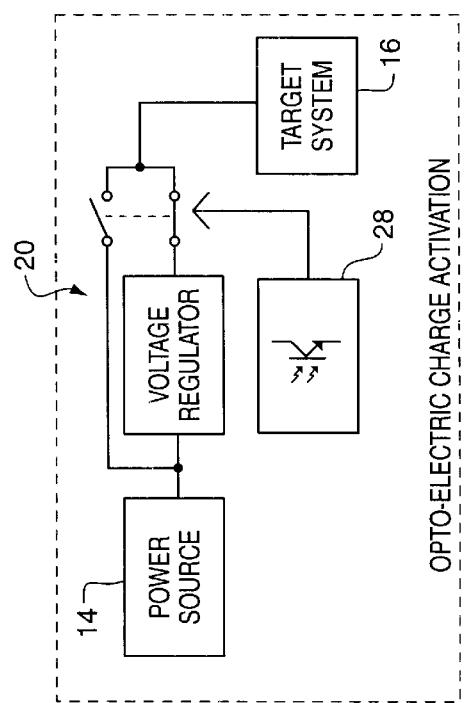
FIG. 6 is a block schematic circuit diagram, similar to the diagram of FIG. 1, of a self contained transportable power source maintenance and charge system which includes an electro-mechanical charge activation system and a latch.

(d) Activation of an electro-mechanical switch and latch circuit 32 including switch 33, latch 34 and switch 36 as shown in FIG. 6

The power source maintenance and charge system 10 is shown in more detail in FIG. 2 and includes an auxiliary power source or battery 14, an optional plug in AC/DC power source 15, a switch 39 for connecting the power source 14 or the power source 15 to the charge maintenance circuit 20 and the magnet 24 operated Reed switch 26. As shown, the charge maintenance circuit 20 includes a voltage regulator 40 coupled between the switch 39 and a pair of series connected transistors 42 and 44. Also connected across the switch 39 are series connected resistor 46 LED 48 and the Reed switch 26. A junction 50 between the resistor 46 and the LED 48 is connected to the P and N gates of the transistors 42 and 44, as shown.

Figure 7:
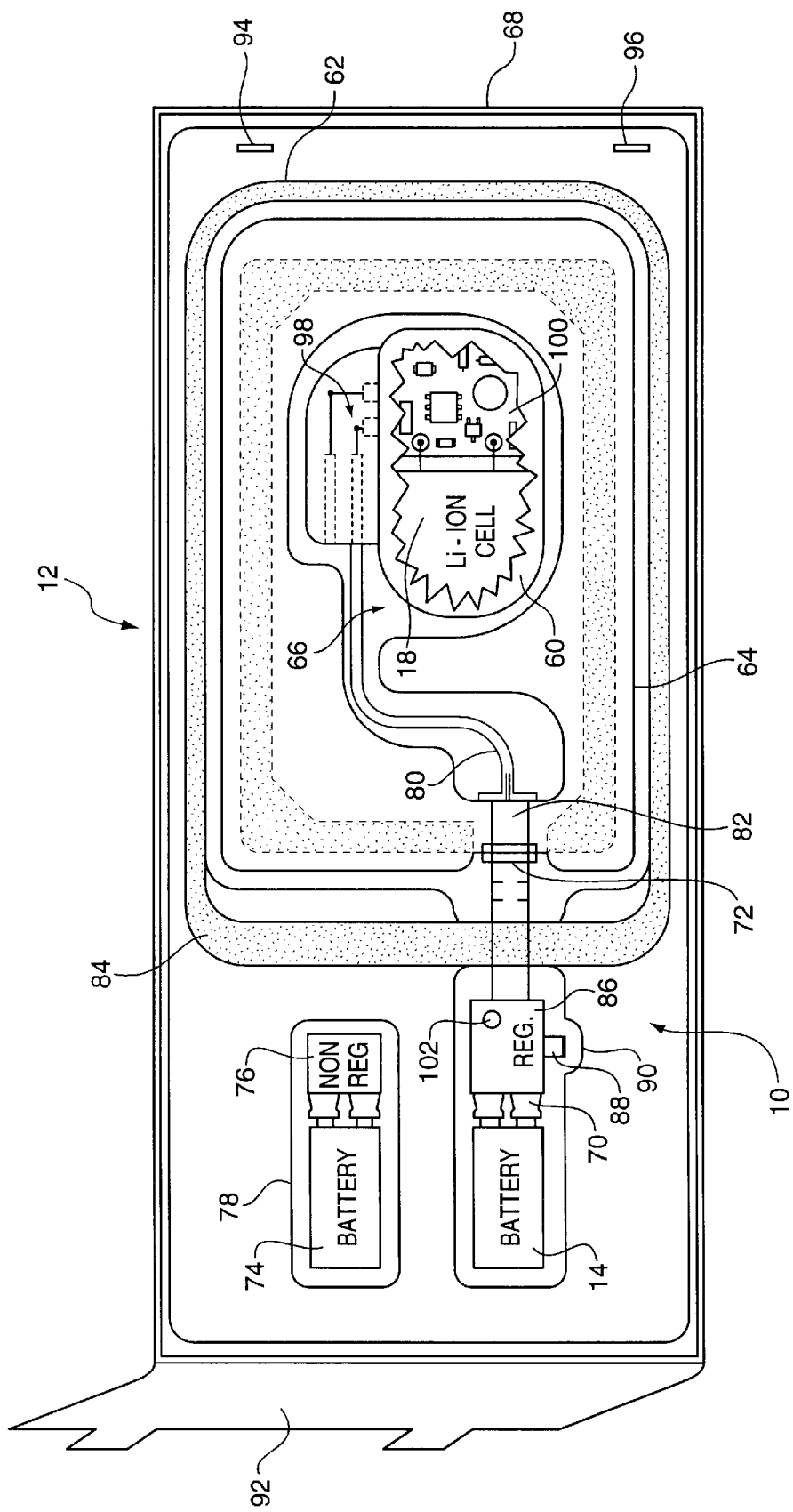
FIG. 7 is a top plan view of part of a blister package for an implantable pulse generator (pacemaker) and a power source maintenance and charge system for maintaining a charge on a lithium ion cell of the pulse generator.

Referring now to FIG. 7, there is shown therein the power source charge and maintenance system 10 for maintaining a charge on a implantable pulse generator 60 which are covered by an outer blister package 62 and inner blister package 64 which incorporates a cavity 66 for retaining the implantable pulse generator 60 in place. A tray or base board 68 mounts the blister packages 62 and 64, the power source or battery 14 which is connected into receptacle 70 which plugs into edge connector pins 72, a spare battery 74 which is connected to a receptacle 76 and fits into a cavity 78 of the tray 68. The tray 68 mounts all of the above components during shipping and storage of the packages 62 and 64.

The implantable pulse generator 60 is connected to a ribbon cable assembly 80 which exits blister packages 62 and 64 through heat seals 82 and 27. The ribbon cable 80 is connected to the 9 volt battery 14 through the electronic module 86 containing the voltage regulator 40, shown in FIG. 3. Electronic module 86 contains push button 88 which is actuated through a dome 90 formed in the blister package 62. A cover 92 of the blister package 62 is folded over tray 68 and locked in place using locking slots 94 and 96.

The voltage regulator 40 in the module 88 will normally deliver a constant voltage to maintain lithium ion cell 18 through ribbon cable assembly 80 connected to a feed through 98 which in turn is connected to an implantable power management system 100. The switch 88 is actuated to provide a charge voltage as required by the lithium ion cell 18. An LED 102 will flash when the regulator 40 in the module 88 is in a charge mode and will turn off when the charge is completed.

Accordingly, the assembly shown in FIG. 7 includes both a target system 16, in this embodiment the implantable pulse generator 60 which is sealed within a double sterile blister package 62, 64, the auxiliary power source 14 and power source maintenance and charge system 10 located in a non-sterile section of the outer blister package 62. This configuration allows the product to be sterilized within an inner blister package 64 of the double blister package 62, 64.

The power maintenance and charge circuit 10 and auxiliary battery 14 may be connected and placed in the outer blister package 62 after sterilization is completed. This method avoids exposing the auxiliary battery 14 and the power maintenance system 10 to the sterilization process.

Figure 8A:
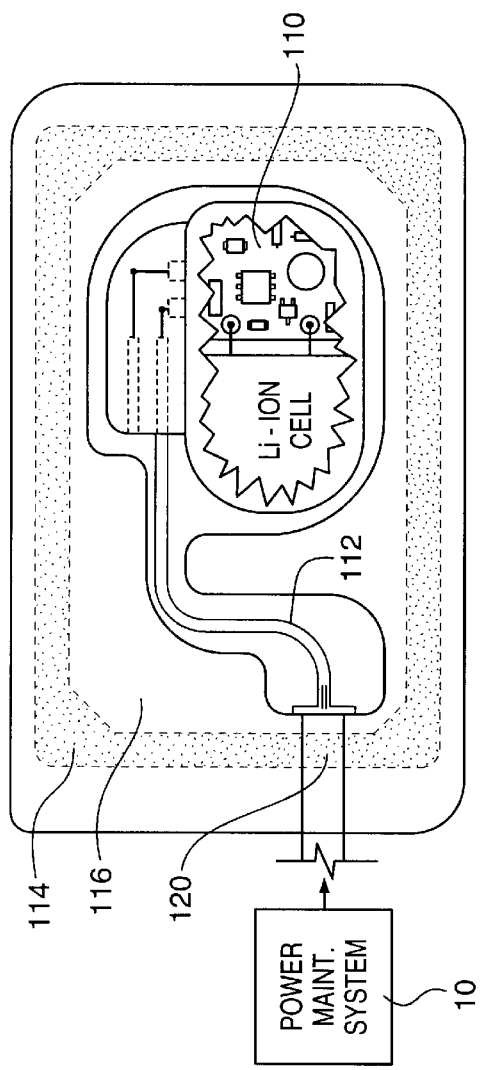
FIG. 8A is a plan view of a blister package without the power source maintenance and charge system and packaging therefor shown in FIG. 7.

As shown in FIG. 8A, the power source maintenance and charge system 10 can be connected to a medical device 110 by means of a flat flexible polymer insulated ribbon cable 112 containing thin metal conductors that pass through a sterile seal area 114 at a seal area 120 in a blister package 116.

Figure 8B:
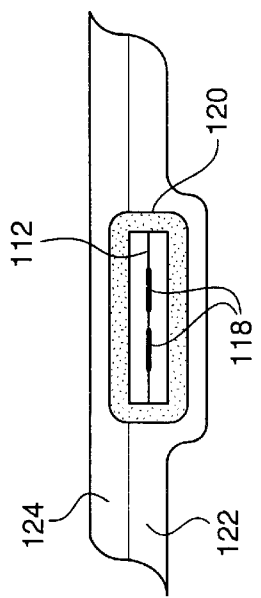
FIG. 8B is an enlarged sectional view of the package area encircled in FIG. 8A.

In FIG. 8B is shown an enlarged cross section of the polymer ribbon cable 112 containing conductors 118 sealed at 120 between the blister material tray or base board 122 and a polymer coated cover 124.

Figure 9:
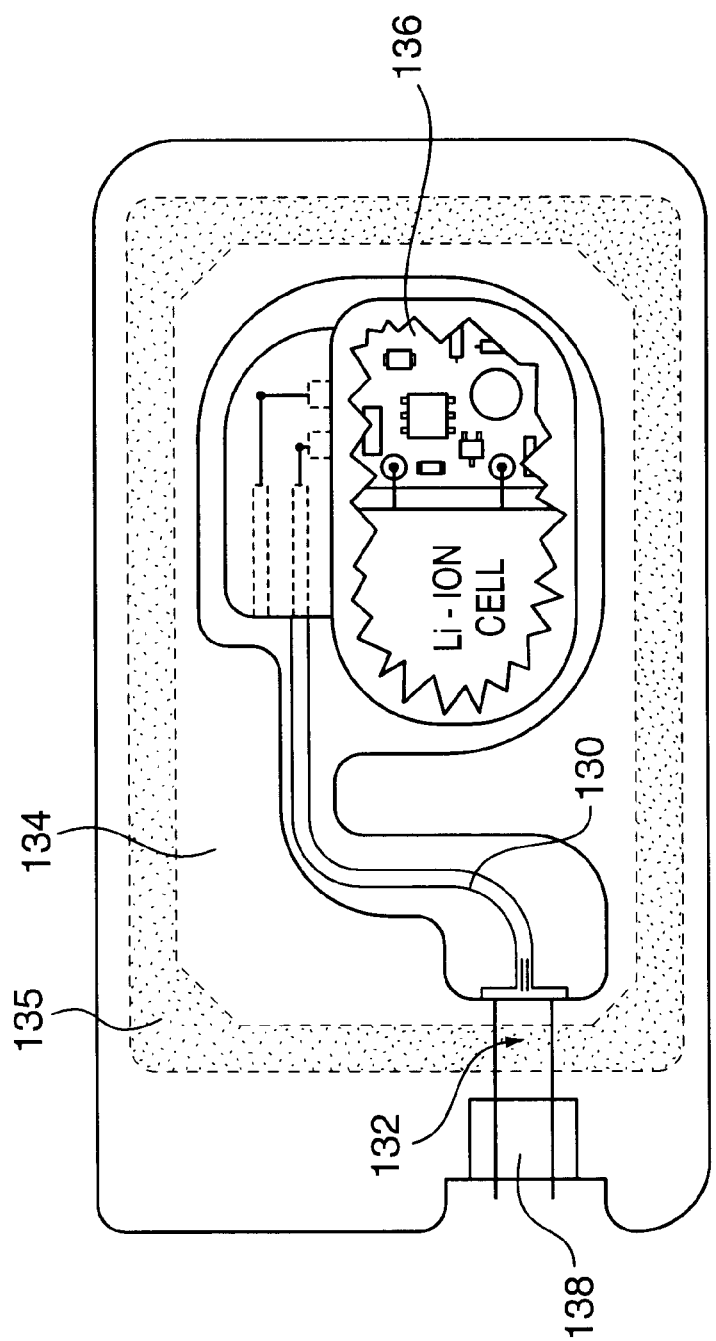
FIG. 9 is a plan view, similar to the view of FIG. 8A, of a blister package including a flat ribbon with conductors which is folded over an edge of the base board of the package.

A polymer insulated flat ribbon 130 (FIG. 9) with metallic conductors is heat fused (sealed) together at a polymer seal area 132 with the blister package tray and a polymer coated cover 134 is sealed in the seal area 135 to the tray to maintain a sterile medical device or other product 136 within safe sterile requirements. The polymer ribbon 130 can be folded over the edge of the blister package as indicated at 138 so as to form an electrical edge connector 138 as shown in FIG. 9.

An electronic module 140 (FIG. 10) that maintains charge on, or charges a, battery 142 can be an integral part of an auxiliary battery connector 144 and equipped with circuitry (not shown) for switching the electronic module 140 to be used in a maintenance or charge mode using a magnetic Reed switch or other means of electronic or electro-mechanical switching to provide current to a pacing lead 146 or a ribbon cable 148 as shown in FIG. 10.

Figures 11A, 11B:
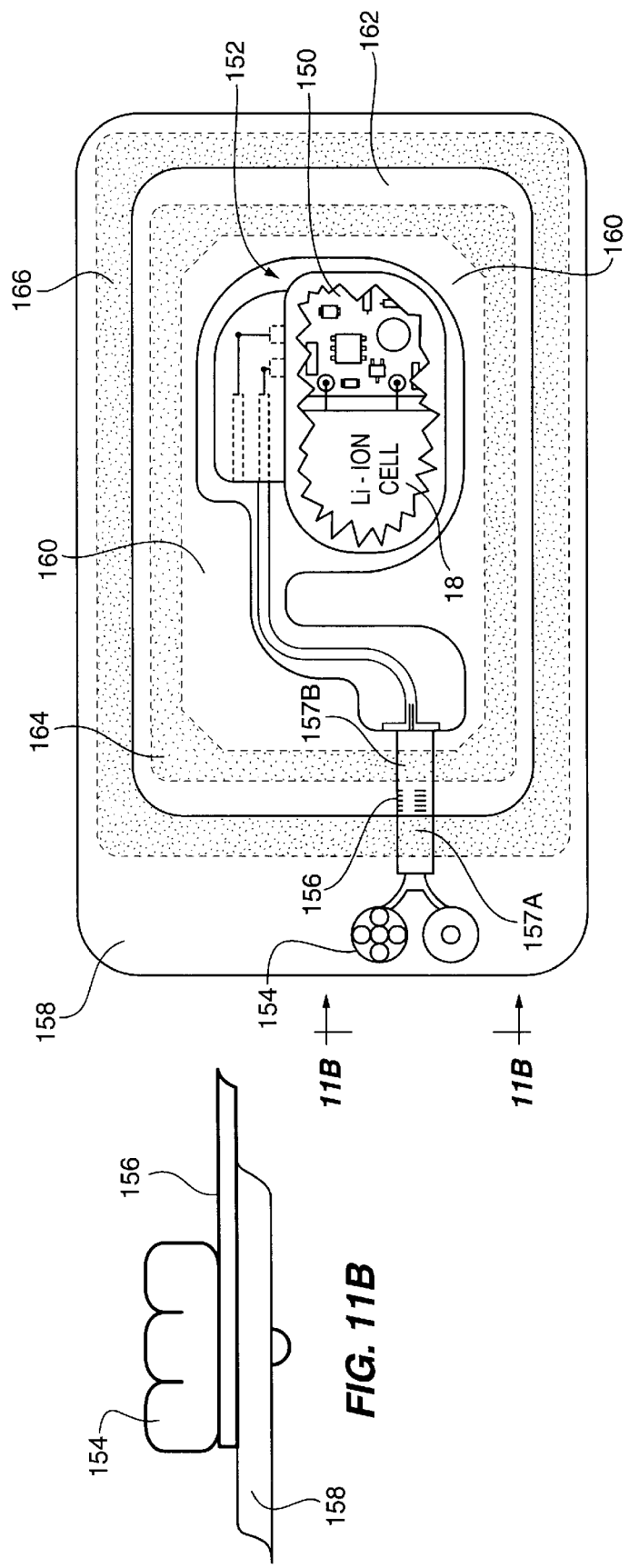
FIG. 11A is a plan view of a blister package wherein the power source maintenance and charge system is incorporated into the medical device within the blister package and the ribbon cable from the package is connected directly to an auxiliary battery of the power source maintenance and charge system.
FIG. 11B is a fragmentary enlarged side view of the base board of the blister package shown in FIG. 11A, is taken along line 11B—11B of FIG. 11A and shows the ribbon cable and the auxiliary battery.

An external electronic module 150 (FIG. 11A) that maintains the charge in the lithium ion cell 18 can also be incorporated within a medical device 152. In this configuration, an auxiliary battery 154 will be connected directly to the medical device 152 using a blister fused ribbon cable 156, sealed at polymer ribbon seals 157A, 157B located on a blister tray 158 having an inner blister 160 and an outer blister 162 sealed to the tray 158 by inner seal area 164 and an outer seal area 166 but without the external electronic module as shown in FIGS. 11A and 11B.

FIGS. 12–15 illustrate various ways of connecting the charge maintenance circuit 20 to a rechargeable cell 18 in a package implantable device or target system 16.

Figure 12:
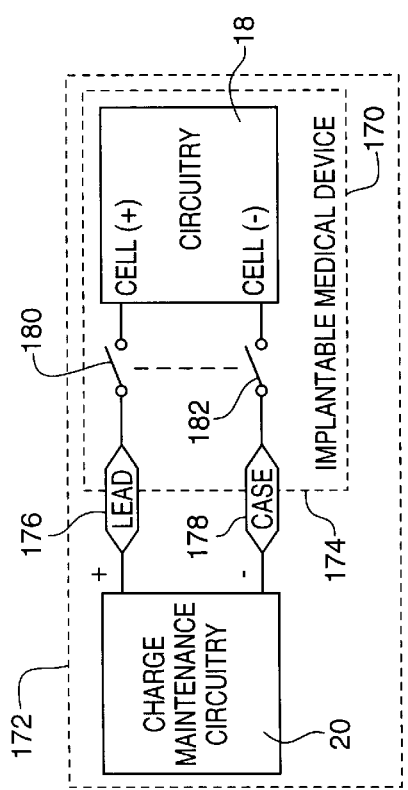
FIG. 12 is a block diagram of a charge maintenance circuit connected via stimulation electrodes and switches to a rechargeable cell.

In FIG. 12 there is shown an inner plastic bubble or cover 170 and an outer plastic bobble or cover 172. Inside the inner plastic cover 170 is the implantable medical device and the rechargeable cell 18. The charge maintenance circuit 20 is mounted on a tray or base (not shown) underneath the outer cover 172. In a sealing area 174 of the inner cover 170 to the tray or base are ribbon lead connectors which in FIG. 12 include a ribbon lead connector 176 from the plus side of the charge maintenance circuit 20 to the implantable lead of the implantable medical device and a ribbon lead connector 178 from the negative output of the charge maintenance circuit 20 to a case of the implantable medical device. The ribbon lead connectors 176 and 178 are connected through tandem switches 180 and 182 to the rechargeable cell 18.

Figure 13:
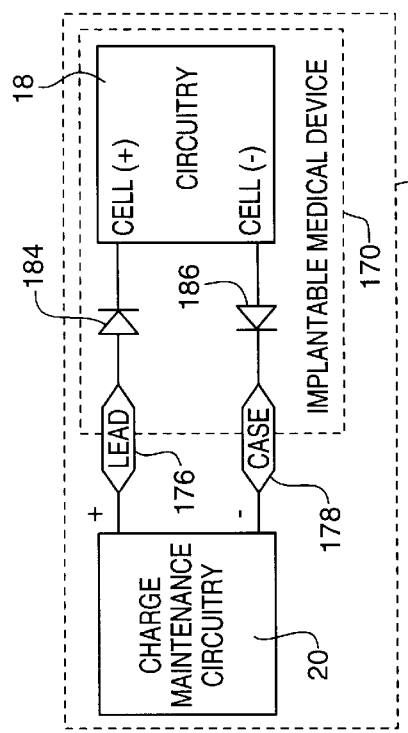
FIG. 13 is a block diagram of a charge maintenance circuit connected via stimulation electrodes and diodes to a rechargeable cell.

The assembly shown in FIG. 13 is substantially identical to the assembly shown in FIG. 12 except that the ribbon lead connectors 176 and 178 are connected to diodes 184 and 186 to the rechargeable cell 18 instead of through tandem switches 180, 182.

Figure 14:
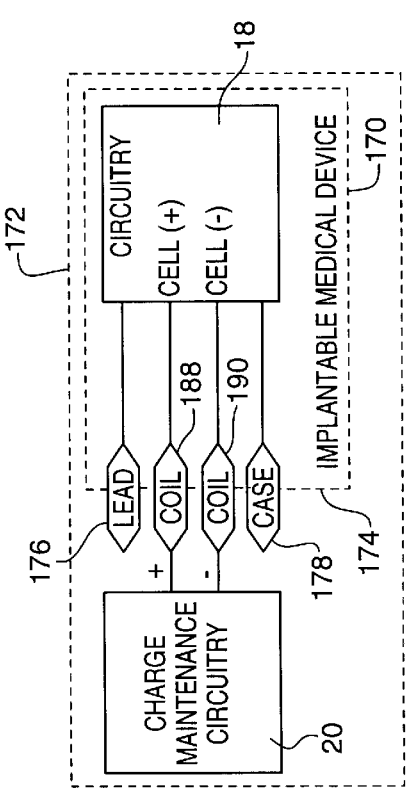
FIG. 14 is a block diagram of a charge maintenance circuit connected via recharging coil lines to a rechargeable cell.

In the assembly shown in FIG. 14, the charge maintenance circuit 20 is connected through recharging coil lines 188 and 190 located in the seal area 174 to the rechargeable cell 18. The lead and case ribbon connectors 176 and 178 remain in the sealed area 174 for testing purposes.

Figure 15:
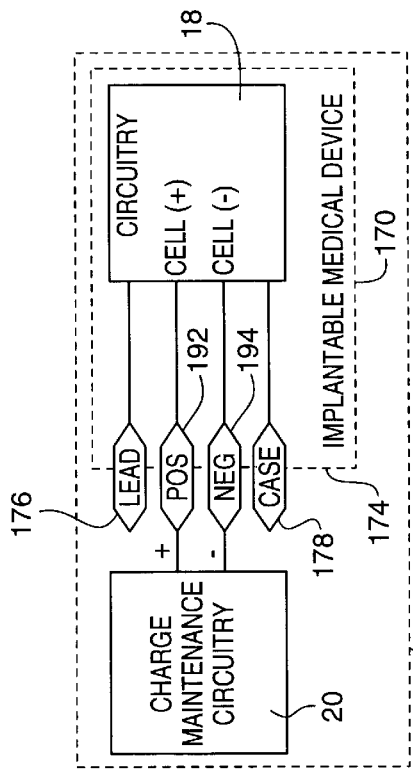
FIG. 15 is a block diagram of a charge maintenance circuit connected directly to a rechargeable cell.

The assembly shown in FIG. 15 is similar to the assembly shown in FIG. 14 except that in place of recharging coil lines 188 and 190 there are provided positive and negative ribbon lead connectors 192 and 194 for connecting the charge maintenance circuit 20 to the rechargeable cell 18 with the lead and case ribbon connectors still located in the sealed area 174.

Figure 16:
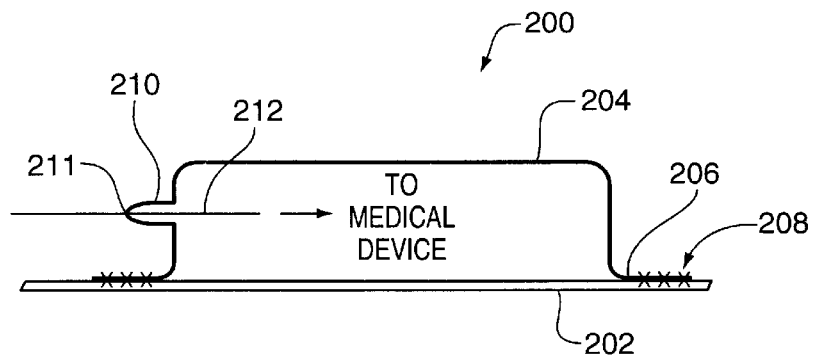
FIG. 16 is a vertical sectional view through a blister package containing another embodiment of the power source maintenance and charge of the present invention and shows a protrusion from a blister cover through which a cable or wire conductors extend for connection to a medical device in the package.

In addition to having a flat or ribbon cable that extends from the blister package along the base or tray of the package, a cable or wire conductors can extend outwardly from the blister package through a protrusion in the blister. In this respect, there is shown in FIG. 16 a blister package 200 including a base or tray 202 and a blister cover 204. The blister cover 204 has a flange 206 which is sealed at 208 to the base 202. A protrusion 210 is formed in the blister package when the blister is formed, and a hole is punched through the protrusion 210 for receiving a cable 212 or other wire conductors for connecting a medical device in the blister package 200 to a power source maintenance and charge system as described above.

Figure 17:
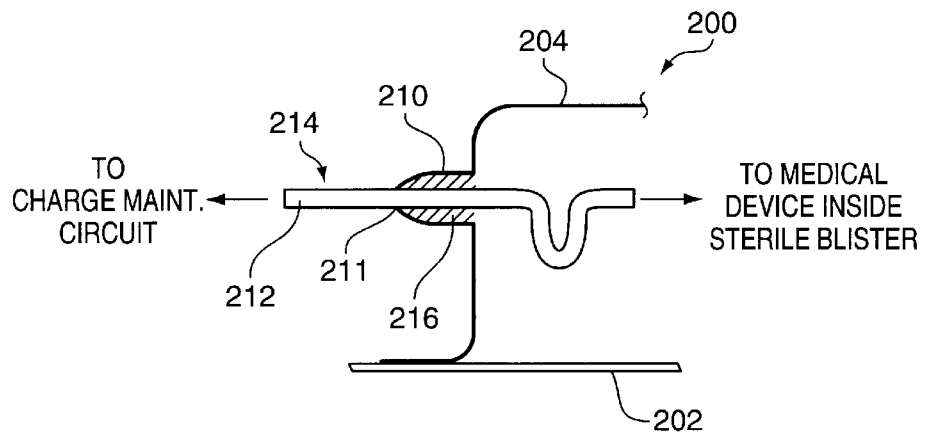
FIG. 17 is a fragmentary vertical sectional view through the blister package shown in FIG. 16 and shows one form of protrusion from a blister cover with an adhesive sealant therein through which a cable or wire conductors extend for connection to the medical device in the package.

Referring now to FIG. 17, there is illustrated therein one form of mounting of the cable 212 in a blister protrusion 210. In this embodiment, the cable 212 extends through the opening 211 in the blister protrusion 210 for connection to a medical device inside the sterile blister package 200. The cable outside the blister protrusion 210 is connected to a cable connector 214 for coupling the cable 212 to a charge maintenance circuit (not shown).

Then, inside the protrusion there is provided an adhesive sealant 216 for sealing the cable within the blister protrusion 210.

Figure 18:
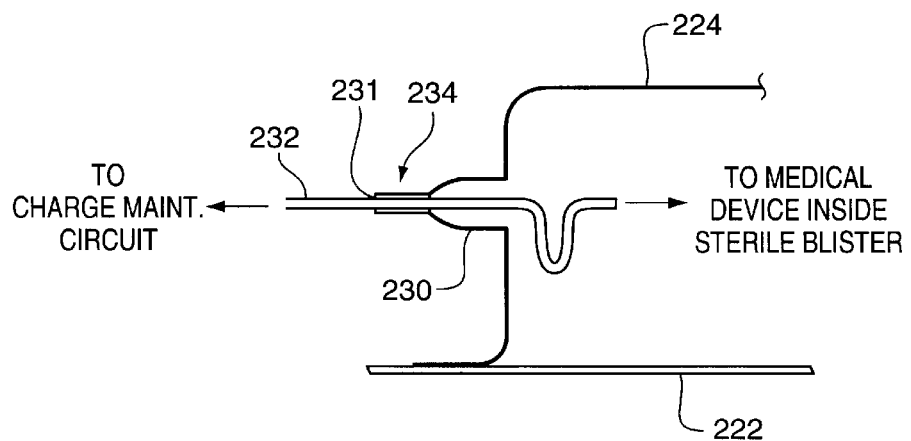
FIG. 18 is a fragmentary vertical sectional view through the blister package shown in FIG. 16 and shows one form of protrusion from a blister cover with a heat seal adhesive therein through which a cable or wire conductors extend for connection to the medical device in the package.

In FIG. 18 there is illustrated a modified blister package 220 which includes a base 222, a blister 224, a blister protrusion 230 having an opening 231 to which a cable 232 extends for connecting a medical device inside the blister package to a charge maintenance circuit. In this embodiment, the blister protrusion 230 is slightly longer than the protrusion 210 and is adapted to be heat sealed to the cable 232, as shown at 234.

From the foregoing description, it will be apparent that the power source maintenance and charge system and method of using same of the present invention have a number of advantages, some of which have described above and others which are inherent in the invention. Also, it will be understood that modifications can be made to the power source maintenance and charge system and method of using same of the present invention without departing from the teachings of the present invention. Accordingly, the scope of the invention is only to be limited as necessitated by the accompanying claims.

We claim:

1. A power source maintenance and charge system and package comprising: a plastic blister package including a base or tray, and an enclosure or blister cover fixed on said base or tray; charge maintenance circuitry mounted on said base or tray outside of said enclosure or cover for maintaining a desired charge on, and for charging, a special power source of an implantable medical device in said package; control means mounted on said base or tray outside of said enclosure or cover for actuating and de-actuating said charge maintenance circuitry; and coupling means for coupling said charge maintenance circuitry to the special power source including a polymer insulated flat ribbon cable that passes into said enclosure or cover through a wall of said enclosure or between said wall and said base or tray of said plastic package containing the device to connect an auxiliary power source, mounted on said base or tray outside of said enclosure or cover and coupled to said charge maintenance circuitry, to the special power source of the device.

2. The power source maintenance and charge system and package of claim 1 wherein the special power source is a lithium ion battery.

3. The power source maintenance and charge system and package of claim 1 wherein said charge maintenance circuitry is integrated into a battery connector which is connected to said auxiliary power source.

4. The power source maintenance and charge system and package of claim 1 wherein said control means for actuating and de-actuating said circuitry includes magnetic switching means for allowing maintenance or charge modes to be switched ON or OFF using a remote magnet to maintain or charge the special power source in the implantable medical device contained within said blister package.

5. The power source maintenance and charge system and package of claim 1 wherein said control means for actuating and de-actuating said circuitry includes an electro-mechanical switch of the control means and said package includes a preformed deflectable dome covering said electro-mechanical switch, said circuitry being activated by pressing or deflecting said preformed dome.

6. The power source maintenance and charge system and package of claim 1 wherein the polymer insulation of said ribbon cable is heat fused between said blister package tray and said blister cover containing the device to create a sealed conductive feedthrough of said ribbon cable that passes into said blister package.

7. The power source maintenance and charge system and package of claim 6 wherein said flat polymer insulated ribbon cable with metallic conductors therein is folded over an edge of said tray to form an edge connector where said cable exits said blister package encasing the device.

8. The power source maintenance and charge system and package of claim 7 wherein said charge maintenance circuitry is connected to said edge connector for coupling said auxiliary power source to the special power source.

9. The power source maintenance and charge system and package of claim 1 wherein said charge maintenance circuitry is mounted within the implantable medical device and said auxiliary power source located outside said enclosure is connected by said circuitry to the special power source in the device.

10. The power source maintenance and charge system and package of claim 9 wherein the polymer insulation of said ribbon cable being heat fused between said blister package tray and said blister cover which form a sealed blister package containing the device to create a sealed conductive feedthrough ribbon cable that passes into said sealed blister package to a battery snap connector of said coupling means to couple said auxiliary power source located on said tray outside of said blister package with a battery snap connector of said coupling means located in an extended flap area outside of a sterile blister seal of said blister package to said ribbon cable thereby to couple said auxiliary power source to the special power source in the device in said blister package.

11. The power source maintenance and charge system and package of claim 1 wherein said charge maintenance circuitry is constructed and arranged to operate, when actuated, in a charge maintenance mode for maintaining a charge on the special power source and a charging mode for charging the special power source to just below a maximum charge value for the special power source.

12. The power source maintenance and charge system and package of claim 1 wherein said coupling means include stimulation electrodes of the implantable medical device and two switches.

13. The power source maintenance and charge system and package of claim 1 wherein said coupling means include stimulation electrodes of the implantable medical device and two diodes.

14. The power source maintenance and charge system and package of claim 1 wherein said coupling means include recharging coil lines between said charge maintenance circuitry and the special power source.

15. The power source maintenance and charge system and package of claim 1 wherein said coupling means include first and second wire conductors directly connected to the special power source.

16. The power source maintenance and charge system and package of claim 1 wherein said package is a sterile package.

17. The power source maintenance and charge system and package of claim 1 wherein said package includes an inner blister cover sealed to said tray over said implantable medical device and within said first named outer blister cover of said package and said flat ribbon cable extends into the space inside said inner blister cover.

18. A power source maintenance and charge system and package comprising: a sealed plastic blister package including a tray and a blister cover; charge maintenance circuitry mounted on said tray outside of said blister cover for maintaining a desired charge on, and for charging, a special power source of a packaged implantable medical device contained in said sealed plastic blister package; control means mounted on said tray outside of said blister cover for actuating and de-actuating said charge maintenance circuitry; coupling means for coupling said circuitry to the special power source including a cable that passes through an opening in said sealed plastic blister package containing the device to connect an auxiliary power source, mounted on said tray outside of said blister cover and coupled to said charge maintenance circuitry, to the special power source of the device; and means for sealing the opening.

19. The power source maintenance and charge system and package of claim 18 wherein said blister cover has a protrusion and the sealed opening is at an outer end of the protrusion.

20. The power source maintenance and charge system and package of claim 19 wherein said protrusion has an adhesive sealant therein for sealing the opening.

21. The power source maintenance and charge system and package of claim 19 wherein the protrusion is heat sealed at an outer end portion thereof to said cable for sealing the opening.

22. The power source maintenance and charge system of claim 18 wherein said package is a sterile package.

23. The power source maintenance and charge system and package of claim 18 wherein said package includes an inner blister cover sealed to said tray over said implantable medical device and within said first named outer blister cover of said package and said flat ribbon cable extends into the space inside said inner blister cover.

* * * * *